(12) United States Patent
Brown

(10) Patent No.: US 6,641,801 B1
(45) Date of Patent: Nov. 4, 2003

(54) GARGLE METHOD TO REDUCE THE DURATION OF COMMON COLD SYMPTOMS

(75) Inventor: Amy Christine Brown, Honolulu, HI (US)

(73) Assignee: Love Lives, Honolulu, HI (US)

( * ) Notice: Subject to any disclaimer, the term of this patent is extended or adjusted under 35 U.S.C. 154(b) by 0 days.

(21) Appl. No.: 09/821,653

(22) Filed: Mar. 28, 2001

Related U.S. Application Data

(60) Provisional application No. 60/194,180, filed on Apr. 3, 2000.

(51) Int. Cl.$^7$ .................. A61K 7/16; A61K 31/045; A61K 35/78; A61F 13/00
(52) U.S. Cl. .................. 424/49; 424/434; 424/435; 424/725; 424/59; 514/724
(58) Field of Search .................. 514/724; 424/725, 424/746, 760, 754, 747, 757, 769, 434, 435, 49, 59

(56) References Cited

U.S. PATENT DOCUMENTS

| | | | |
|---|---|---|---|
| 4,469,674 A | * | 9/1984 | Shah et al. |
| 4,523,589 A | * | 6/1985 | Krauser |
| 5,455,023 A | * | 10/1995 | Giacin et al. |
| 5,468,500 A | * | 11/1995 | Rodriguez-Flores et al. |
| 6,037,327 A | * | 3/2000 | Castillo et al. |
| 6,165,494 A | * | 12/2000 | Picciano |
| 6,169,118 B1 | * | 1/2001 | Bilali |
| 6,348,187 B1 | * | 2/2002 | Pan et al. |
| 6,447,816 B1 | * | 9/2002 | Vail, III et al. |

OTHER PUBLICATIONS

Evans, A. 1989. Viral Infections of Humans, Epidemiology and Control, 3rd ed. Penum Med. Book Co., NY. p. 593.*
Website Drugstore.com titled Listerine Antiseptic Mouthwash, Coll Mint, 4 pages, original copyright 1999.*
Barrett, S. Homeopathy: The Ultimate Fake, Aug. 1999, 6 pages, obtained from quackwatch.com website.*

* cited by examiner

Primary Examiner—Christopher R. Tate
(74) Attorney, Agent, or Firm—The Webb Law Firm

(57) ABSTRACT

The common cold is caused by a virus. Antiviral compounds that kill viruses would then be most likely to serve as a remedy for the common cold. This invention seeks to offer a unique use of an antiviral agent, ethanol (with or without additional homeopathic and/or herb ingredients) through the unique topical application of a mouthwash to a sore throat that is often the first symptom of a common cold. The sore throat is caused by the virus setting up to enter the body after which a cascade of immune response symptoms will occur. Current cold remedies do nothing but treat these immune response symptoms. This invention is unique in that it destroys the virus directly, blocking the cold virus at its point of entry, and the remaining cold symptoms never appear. It does not matter how many cold viruses exist, because the antiviral nature of ethanol kills viruses upon contact. This is the first time that treatment of a sore-throat with antiviral agents (ethanol with or without additional homeopathic and/or herb ingredients) is being used to effectively block the common cold. Research testing this common cold remedy have shown it to be effective in 18 out of 20 case studies, and a double-blind, placebo controlled clinical trial is being conducted.

7 Claims, No Drawings

GARGLE METHOD TO REDUCE THE DURATION OF COMMON COLD SYMPTOMS

This application claims the benefit of provisional application No. 60/194,180, filed Apr. 3, 2000.

CROSS REFERENCES TO RELATED APPLICATIONS

| U.S. Pat. Documents | | |
|---|---|---|
| 3852432 | December 1974 | Henkin |
| 3864472 | February 1975 | Pensak |
| 3876759 | April 1975 | Pensak |
| 3888976 | June 1975 | Mikyvy |
| 4059686 | November 1977 | Tanaka |
| 4130638 | December 1978 | Dhabhar |
| 4150151 | April 1979 | Pader |
| 4255419 | March 1981 | Leopold |
| 4292324 | September 1981 | Jonsson |
| 4420471 | December 1983 | Elton |
| 4523589 | June 1985 | Krauser |
| 4503070 | March 1985 | Eby |
| 4684528 | August 1987 | Godfrey |
| 4708949 | November 1987 | Liu |
| 4814163 | March 1989 | Barth |
| 4814164 | March 1989 | Barth |
| 4946688 | August 1990 | Fahim |
| 4956385 | September 1990 | Eby |
| RE033465 | November 1990 | Eby |
| 5002970 | March 1991 | Eby |
| 5112617 | May 1992 | Criscudo |
| 5240694 | August 1993 | Gwaltney |
| 5286748 | February 1994 | Eby |
| 5409905 | April 1995 | Eby |
| 5422097 | June 1995 | Gwaltney |
| 5492689 | February 1996 | Gwaltney |
| 5626831 | May 1997 | Van Moerkerken |
| 5622724 | April 1997 | Bryce-Smith |

STATEMENT REGARDING FED SPONSORED R & D

This invention was not supported or associated with any federally sponsored research and/or development project or funds.

OTHER REFERENCES

Eby et al. Antimicrobrial Agents and Chemother 1984;25:20–24.
Garland M L, O Hagmeyer K. Ann Pharmacother 1998;32:63–69.
Godfrey J C et al. J Intl Med Res 1992;20:234–246.
Godfrey J C. Antimicrobrial Agents and Chemother 1988;32:605.
Korant B D et al. Nature 1974;248:588–590.
Macknin M L et al. JAMA 1998;279:1962–1967.
Mossad S B et al. Ann Intem Med 1996;125:81–88.
Turner R B. Ann Alergy Asthma Immunol 1997;78:531–540.
van kempen M et al. +i Rhinology 1999;37(3):97–103 . . .

BACKGROUND OF THE INVENTION

1. Field of Invention

This invention relates to methods and preparations for reducing the duration of common colds and reducing the severity of common cold symptoms. More particularly, this invention relates to the remedies comprising medicaments, which shorten the duration of common colds, reduce the severity of symptoms, and/or otherwise beneficially treat common colds. These ingredients are believed to be antiviral agents. Such ingredients are combined with a pharmaceutically acceptable carrier suitable for the chosen method and form of administration. The most preferred method of administration is exposure of the oral and oral pharyngeal tissues to the agents for a period of time sufficient for the remedy to be exposed to the oral and oral pharyngeal mucous membranes. The preferred forms of the remedy for administration therefore include mouthwashes and lozenges. In these embodiments, the preparation preferably includes a suitable carrier, and other ingredients such as flavors, stabilizers, lubricants, and additional natural or artificial sweeteners.

2. General Background

The "common cold" and, simply, "cold" are time-honored phrases used by both physicians and lay persons alike for the identification of upper respiratory illness caused by viral infection. Colds are most often acute, minor illnesses which eventually subside without treatment for the infection itself. However, common colds are still a major public health problem.

Colds are the most common acute illness in the United States and account for about one-half of all absences from school and work. Viruses that cause the common cold are easily transmitted from host to host. For example, such viruses may be spread in aerosols, so they may be spread through the air by, e.g., sneezing. Additionally, the viruses can survive out of a host's body for extended periods of time, and so can be transmitted by hands and objects. Further, a virus that causes only a minor cold in one host may threaten the life of another host by causing influenza, a much more serious upper respiratory infection that may be fatal. P. R. Murray et al., *Medical Microbiology*, $2^{nd}$ ed., Mosby-Year Book, Inc., p. 723,616–7 (1994).

Since the discovery of rhinovirus in 1956, a considerable body of knowledge has been acquired on the etiology and epidemiology of common colds. It is known that the common cold is not a single entity, but rather is a group of diseases caused by members of several families of viruses including adenoviruses, influenza viruses, parainfluenza viruses, rhinoviruses, respiratory syncytial viruses, enteroviruses, echoviruses, coxsackieviruses, and coronaviruses. Much work has been performed in characterizing viruses which cause the common cold. For instance, the molecular biology of rhinoviruses, which causes at least 50% of all upper respiratory tract infections, is understood in great detail. Murray, pp. 723,616

In contrast, progress on the treatment of common colds has been slow despite these advances. Indeed, it has been believed that the only current cure for the common cold is the body's natural defenses and the passage of time.

Many over-the-counter remedies for the common cold only treat symptoms. There are over 200 different virus serotypes that can cause the common cold. For example, there are at least 100 serotypes of rhinoviruses alone. Murray p. 616, Rhinology 37(3):97–103, 1999. It is therefore not possible to build immunity to this many causes of the common cold. It is also difficult to develop remedies that are effective against such a large number of viruses. Therefore, symptomatic relief has been the traditional recourse.

These prescription or over-the-counter products which treat symptoms of the common cold usually contain one or more of the following drugs: antihistamines, decongestants, pain relievers (aspirin, acetaminophen, ibuprofen), cough suppressants, expectorants, and analgesics. These remedies do not reduce the duration of the common cold, are of limited effectiveness in relieving the symptoms of the cold, and are often accompanied by unwelcomed side effects.

The duration of the average cold varies greatly among individuals. Twenty-five percent of all colds last 14 days, but the average duration of a cold is 7 days, with or without treatment.

Treatment with interferon has been somewhat successful in limiting the progression of infection in common colds. However, interferon has many negative effects and cannot be administered for any length of time. Murray pp. 616–619.

Zinc ions have been reported to inhibit the replication of rhinoviruses. See, Korant B D et al., Nature 248:588–590 (1974). Recently, soluble and ionizable zinc compounds applied to the oral and oralpharyngeal mucosa have been used to treat common colds and have had some success in shortening the duration of the common cold. See, for example, U.S. Pat. Nos. 5,409,905; 5,286,748; 5,286,748; RE033465; and 4,956,385; to Eby Ill. See also U.S. Pat. No. 5,622,724 to Bryce-Smith and U.S. Pat. No. 4,684,528 to Godfrey. Eby claims that after seven days, 86% of 37 zinc-treated subjects were asymptomatic, compared with only 46% of 28 placebo-treated subjects. (Antimicrob. Agents Chemother. 25(1):20–4, 1984). Mossad's double-blind, placebo controlled study on zinc lozenges revealed that patients treated with zinc lozenges had colds averaging 4.4 days compared to 7.6 days for those on the placebo. (Ann Intem Med 125::81–88, 1996). However, treatment also causes side effects, such as nausea and bad-taste reactions. Mossad. The cold duration thus appears reduced by zinc treatment, but the reduction is not dramatic, especially given the average cold duration of 7 days.

Given the very limited success of current cold remedies, some people say that cold remedies today come no closer to curing the common cold than they did thousands of years ago. Thus there can be no question as to the need for an improved remedy that will shorten the duration of common colds.

SUMMARY OF THE INVENTION

This invention provides methods and compounds for reducing the presence, duration, and severity of a common cold and of its symptoms by the administration of ethanol with or without homeopathic and/or herbal medicaments.

It is an object of this invention to provide effective treatments for the treatment of the common cold and its symptoms. Specifically, it is an object of this invention to provide remedies which reduce the duration of the cold, which reduce the severity or duration of one or more symptoms of the cold, and/or which prevent the common cold.

It is another object of this invention to overcome the problems and disadvantages associated with currently known approaches to treating the common cold and its symptoms.

Prior treatments for the cold have focused on alleviation of its symptoms. Very few remedies have had any success in reducing the duration of the cold. Further, prior treatments almost always contain drugs which cause side effects, which can be as debilitating as the cold itself. Unexpectedly, the present inventor has discovered that certain medicaments (ethanol with or without homeopathic and/or herb ingredients) can reduce the duration of the cold itself, as well as reducing the severity of the symptoms of the cold, and may also prevent infection by cold viruses. The remedy's active ingredient is ethanol with or without homeopathic and/or herb ingredients that are without known side effects and/or are given at homeopathic dosages, which appear to produce no side effects. The remedies of this invention therefore represent a novel treatment for the common cold, which treatment overcomes many of the disadvantages of the prior remedies.

In one embodiment, remedies according to the present invention include homeopathic concentrations of *Allium cepa* (red onion), *Salvia officinalis* (Sage), *Sambucus nigra* (elderberry), Capsicum (cayenne fruit), *Mentha piperta* (peppermint), and/or *Thymus serpyllum* (thyme); and also include perhaps one or a combination of the following ingredients: *Olea europaea* (olive whole leaf) *Lomatium dissectum* (lomatium root), *Rubis idaeus* (red raspberry leaf), and/or *Commiphora myrrha* (mrryh), *Trigonella foenum-graecum* (Fenugreek), *Pulmonaeia officinalis* (lungwort), *Althea officinalis* (marshmallow root tea), *Glycyrrhiza glabra* (licorice), *Ulmus rubra* (slippery elm bark), *Tabebuia avellanedae* (Pau d'arco), *Thymus vulgaeis* (thyme), *Melissa officinalis* (lemon oil), *Allium sativum* (garlic), and/or *capsicum annuum* (cayenne fruit).

In a preferred embodiment, remedies according to the present invention include homeopathic concentrations of *Allium cepa* (red onion), *Salvia officinalis* (Sage), *Sambucus nigra* (elderberry), Capsicum (cayenne fruit), *Mentha piperita* (peppermint), and/or *Thymus serpyllum* (thyme); and may also include one or a combination of *Olea europaea* (olive whole leaf), *Lomatium dissectum* (lomatium root), *Rubis idaeus* (red raspberry leaf), and/or *Commiphora myrrha* (mrryh).

In another preferred embodiment, the remedies comprise homeopathic concentrations singly and/or in combination of *Allium cepa* (red onion), *Salvia officinalis* (Sage), *Sambucus nigra* (elderberry), Capsicum (cayenne fruit), *Mentha piperita* (peppermint), *Thymus serpyllum* (thyme), and/or olive whole leaf (*Olea eruopaea*).

In yet another preferred embodiment, the remedies according to the present invention comprise one or a combination of *Olea europaea* (olive whole leaf), *Lomatium dissectum* (lomatium root), *Rubis idaeus* (red raspberry leaf), and/or *Commiphora myrrha* (mrryh).

In a particularly preferred embodiment, the remedies according to the present invention comprise homeopathic concentrations of at least one of Allium cepa (red onion), *Salvia officinalis* (Sage), *Sambucus nigra* (elderberry), Capsicum (cayenne fruit), *Mentha pipefita* (peppermint), and/or *Thymus serpyllum* (thyme) and also comprise at least one of *Olea europaea* (olive whole leaf), *Lomatium dissectum* (lomatium root), *Rubis idaeus* (red raspberry leaf), and/or *Commiphora myrrha* (mrryh).

In another particularly preferred embodiment, the remedies according to the present invention comprise homeopathic concentrations of *Allium cepa* (red onion), *Salvia officinalis* (Sage), *Sambucus nigra* (elderberry), Capsicum (cayenne fruit), *Mentha piperita* (peppermint), and/or *Thymus serpyllum* (thyme) and also comprise *Olea europaea* (olive whole leaf), *Lomatium dissectum* (lomatium root), *Rubis idaeus* (red raspberry leaf), and/or *Commiphora myrrha* (mrryh).

In a very particularly preferred embodiment, the remedy according to the present invention comprises sufficient concentrations of ethanol.

In a preferred embodiment, the remedy is provided in a form that is not ingested into the digestive system, but instead facilitates contact between the active agents and the tissues in which the virus is present or through which the virus is likely to enter the body.

In a preferred embodiment, the remedy is administered in the form of nasal spray. This form of provides topical application of the medicaments to the nasal mucosa.

In another preferred embodiment, the remedy is administered in the form of a throat spray. This form of provides topical application of the medicaments to the oral pharyngeal mucosa.

In a particularly preferred embodiment, the remedy administered is in the form of a mouthwash. This form provides topical application of the medicaments to the mouth and throat (specifically, the oral and oral pharyngeal mucosa).

In another particularly preferred embodiment the remedy administered in the form of a lozenge or troche. This form provides topical application of the medicaments to the mouth and/or throat (specifically, the oral and oral pharyngeal mucosa).

In one embodiment, the medicament is applied with a frequency and/or at a dosage which results in the reduction of the duration of the cold.

In another embodiment, the medicament is applied with a frequency and/or at a dosage which results in the reduction of the severity or presence of one or more symptoms of the cold.

In yet another embodiment, the medicament is maintained in contact with the mouth and/or throat for a sufficient length of time that reduction of the duration of the cold is achieved.

In still another embodiment, the medicament is maintained in contact with the mouth and/or throat for a sufficient length of time that reduction of the severity or presence of one or more symptoms of the cold is achieved.

In still another embodiment, the medicament is maintained in contact with the mouth and/or throat for a sufficient length of time that infection by cold viruses is prevented.

In a related embodiment, the maintenance of contact is achieved through the gargling of a mouthwash for a suitable length of time.

In another related embodiment, the maintenance of contact is achieved by the slow dissolution in the mouth of a suitably sized lozenge.

In other embodiments, the remedy may be administered in the form of a sublingual or buccal tablet, a syrup, or sublingual liquid drops or pastilles.

In yet other embodiments, the remedy is administered in a form that is ingested into the digestive tract, such as tablets, capsules, and liquids.

In still another embodiment, the remedy is administered in the form absorbable through the skin.

DETAILED DESCRIPTION OF THE INVENTION

The remedies of the present invention comprise ethanol with or without homeopathic and/or herbal ingredients. The remedies of the present invention preferably do not contain any drugs such as antihistamines, decongestants, pain relievers (e.g., aspirin, acetaminophen, ibuprofen), cough suppressants, expectorants, and analgesics. Consequently, the remedies of the present invention also do not produce the side-effects associated with the use of such drugs. Further, the remedies of the present invention are preferably administered in a form which facilitates contact between the active agents and the tissues in which the virus is present. Thus, the remedies of the present invention are preferably not ingested into the digestive system, which is a further reason that the present remedies have not been associated with any side-effects.

Unlike previous remedies, including zinc lozenges, the remedy of the present invention shows a dramatic blockage of cold symptoms within 12–48 hours of illness. The first 12 to 24 hours of a cold is often unavoidable, as this is the time that patients realize that a cold is actually present or on the way. The remedy of the present invention causes the symptoms to begin to gradually subside as the body's natural immune system is bolstered to block the virus invasion. In many cases, a dramatic or complete blockage of the symptoms is effected within 12 to 24 hours of using the remedy of the present invention.

Remedies according to the present invention may include homeopathic concentrations of one or a combination of *Allium cepa* (red onion), *Salvia officinalis* (Sage), *Sambucus nigra* (elderberry), Capsicum (cayenne fruit), *Mentha piperita* (peppermint), *Thymus serpyllum* (thyme), *Aconitum napellus* (monkshood), *Allium sativum* (garlic), *Anas barbariae* (Oscillococcinum), *Euphrasia officinalis* (eyebright), *Ferrum phosphoricum* (ferrous hydrophosphate), *Gelsemium sempervirens* (yellow jassmine), *Kali bichromicum* (potassium dichromate), *Natrum muriaticum* (sodium chloride), *Phytolacca decandra* (poke), *Pulsatilla nigricans* (wind flower), and/or Sulphur (sulphur); and may also include *Olea europaea* (olive whole leaf), *Lomatium dissectum* (lomatium root), *Rubis idaeus* (red raspberry leaf, and/or *Commiphora myrrha* (mrryh), *Trigonella foenumgraecum* (Fenugreek), *Pulmonana officinalis* (lungwort), *Althea officinalis* (marshmellow root tea), *Glycyrrhiza glabra* (licorice), *Ulmus rubra* (slippery elm bark), *Tabebuia avellanedae* (Pau d'arco), *Thymus vulgaris* (thyme), *Melissa officinalis* (lemon oil), *Allium sativum* (garlic), *capsicum annuum* (cayenne fruit). Preferably, remedies according to the present invention include homeopathic concentrations of *Allium cepa* (red onion), *Salvia officinalis* (Sage), *Sambucus nigra* (elderberry), Capsicum (cayenne fruit), *Mentha piperita* (peppermint), and/or *Thymus serpyllum* (thyme); and also include *Olea europaea* (olive whole leaf), *Lomatium dissectum* (lomatium root), *Rubis idaeus* (red raspberry leaf), and/or *Commiphora myrrha* (mrryh). Even more preferably, the remedies comprise homeopathic concentrations of at least one of *Allium cepa* (red onion), *Salvia officinalis* (Sage), *Sambucus nigra* (elderberry), Capsicum (cayenne fruit), *Mentha pipenta* (peppermint), and/or *Thymus serpyllum* (thyme). Remedies typically also comprise at least one of *Olea europaea* (olive whole leaf), *Lomatium dissectum* (lomatium root), *Rubis idaeus* (red raspberry leaf), and/or *Commiphora myrrha* (mrryh). Most preferably, the remedies of the present invention comprise homeopathic concentration of at least one of *Allium cepa* (red onion), *Salvia officinalis* (Sage), *Sambucus nigra* (elderberry), Capsicum (cayenne fruit), *Mentha piperita* (peppermint), and *Thymus serpyllum* (thyme), and at least one of *Olea europaea* (olive whole leaf), *Lomatium dissectum* (lomatium root), *Rubis idaeus* (red raspberry leaf), and/or *Commiphora myrrha* (mrryh).

When *Allium cepa* (red onion), *Salvia officinalis* (Sage), *Sambucus nigra* (elderberry), Capsicum (cayenne fruit), *Mentha pipenta* (peppermint), *Thymus serpyllum* (thyme), *Aconitum napellus* (monkshood), *Allium sativum* (garlic), *Anas barbariae* (Oscillococcinum), *Euphrasia officinalis* (eyebright), *Ferrum phosphoricum* (ferrous hydrophosphate), *Gelsemium sempervirens* (yellow jassmine), *Kali bichromicum* (potassium dichromate),

*Natrum muriaticum* (sodium chloride), *Phytolacca decandra* (poke), *Pulsatilla nigricans* (wind flower), and/or Sulphur (sulphur) are included in the remedies of this invention, each of these ingredients is preferably prepared to homeopathic concentrations, preferably at a concentration of 1× to 60 C, and more preferably at a concentration of from 30× to 1×. Typically, the concentration is 30× or 30C, and most preferably the concentration is 30C. Preparation of homeopathic ingredients is preferably accomplished through successive dilutions and potentiations, and is well within the ability of one skilled in the art of homeopathy. The prepared homeopathic ingredients are preferably included in the formulation of remedies according to the present invention.

When *Olea europaea* (olive whole leaf), *Lomatium dissectum* (lomatium root), *Rubis idaeus* (red raspberry leaf, and/or *Commiphora myrrha* (mrryh), *Trigonella foenumgraecum* (Fenugreek), *Pulmonana officinalis* (lungwort), *Althea officinalis* (marshmallow root tea), *Glycyrrhiza glabra* (licorice), *Ulmus rubra* (slippery elm bark), *Tabebuia avellanedae* (Pau d'arco), *Thymus vulgaris* (thyme), *Melissa officinalis* (lemon oil), *Allium sativum* (garlic), and/or *capsicum annuum* (cayenne fruit) are included in the remedies of this invention, any of these ingredients may be included at a concentration of from 0.01 to 10% w/v of the remedy. Preferably, any of these ingredients is included at a concentration of 0.1% to 5% w/v of the remedy. Even more preferably, any of these ingredients is included at a concentration of 0.5 to 1% w/v of the remedy. Typically, any of these ingredients is included at a concentration of 1% w/v of the remedy.

Ethanol is included as the base in which homeopathic and/or herbal ingredients may or may not be included and its concentration will range from 20 to 95% w/v. Preferably any food grade or consumer digestible ethanol or spirit ethanol (gin, rum, vodka, etc.) will suffice. Even more preferably, are any of these ingredients at 27 to 40% ethanol (ethanol). Very preferably, the ethanol of choice is vodka with at least a 31 to 37% ethanol content.

These medicaments (ethanol with or without homeopathic and/or herb ingredients extracted and stored in vodka or similar ethanol source), comprise the remedies of the present invention. It is within the ability of one skilled in the art of homeopathy, herbal therapy or supplementation, pharmacology, and/or clinical medicine to optimize the dosage amount, potency, and frequency of administration in order to accomplish objects such as reducing the duration of a cold, reducing the severity of the symptoms of a cold, and/or preventing infection by a cold virus. It is also recognized that these values may differ with such factors as age, weight, and immune status of the subject, severity of illness, and whether the remedy is desired to be used as a treatment for an existing illness or as a prophylaxis.

Other homeopathic and/or herbal medicaments may optionally be included in the remedies of the present invention. It is recognized that non-homeopathic drugs which are commonly used to treat cold symptoms, such as drugs such as antihistamines, decongestants, pain relievers (e.g., aspirin, acetaminophen, ibuprofen), cough suppressants, expectorants, and analgesics, may also be included in the remedies of the present invention. However, preferably, the remedies of the present invention do not contain non-homeopathic drugs.

Preferably, the remedies do not contain any drugs which are not included in the Homeopathic Pharmacopoeia of the United States, or herb or ethanol ingredients that have been used for centuries. Preferably, the remedies do not contain any substances or amounts of substances which require evaluation under an NDA (New Drug Application). The term "drug" is not meant to encompass substances which are herbal or are considered to be foods or dietary supplements by the FDA. Additionally, the term "drug" is not meant to encompass homeopathic concentrations of substances for which an NDA would be required by the FDA in larger concentrations. Homeopathic remedies may exceed 10% ethanol since ethanol is a key ingredient in the manufacturing process.

The remedies of the present invention preferably do not include interferon, interferon inducers, propanediamine, enviroxime, dichloroflaven, 2{(1,5101-tetrahydro-3H-thiazolo[3,4b]isoquinolin-3-ylidene)amino}-4-thiazoleacetic acid (S) or sodium polyacrylate. Most preferably, the remedies do not contain these substances at any concentration, i.e., most preferably, these substances are absent from the remedies.

A "common cold" or simply "cold" is that condition generally associated with the term, including any or all symptoms thereof, such as nasal drainage, nasal congestion, headache, fever, myalgia, sneezing, sore throat, scratchy throat, cough and hoarseness, and, occasionally, bronchial-sinusitis symptoms. A sore throat is commonly the first sign that a subject has been infected by a cold virus and is a sign that the virus has lodged itself in the tender throat lining. The virus grows through the surface to the sensitive nerve endings resulting in inflammation and soreness. Mucus flow increases trying to sluff the throat irritant away, but the mucus and the debris from the dead cells drop down into the lungs, spreading the virus and resulting in further symptoms, such as a hacking cough. Post nasal drip follows. Swelling in the back of the throat can also block Eustachian tubes making it difficult to hear. Unfortunately, some individuals suffer more seriously from colds. Sinuses may become blocked by the excessive swelling of membranes resulting in a severe sinus headache. If recovery is delayed and the virus spreads to the lungs bronchitis may develop, and may, especially in immune-compromised individuals, turn into pneumonia . . . a potential cause of death.

For the purposes of this disclosure, a subject who is described as "suffering from a cold" is equivalent to a subject who is described as "suffering from the symptoms of a cold," and both phrases refer to a subject who is experiencing some or all of the above-listed symptoms of the common cold.

The preparations of the invention are suitable for the treatment of an infection by a virus generally recognized as causing, or being associated with, the common cold or the symptoms thereof. The common cold is most commonly caused by rhinoviruses, and the second leading cause of the common cold are the coronaviruses. Other types of virus recognized as causing or being associated with the common cold include adenoviruses, influenza viruses, parainfluenza viruses, respiratory syncytial viruses, enteroviruses, echoviruses, and coxsackieviruses.

While it is believed that the preparations of the invention are actually virostatic or viricidal, it will be appreciated that this is not known for certain, and it is possible that only symptomatic relief is obtained. Specifically, without wanting to be limited to a specific theory or mechanism of action of the remedies of the present invention, the inventor believes that the remedies function by killing the virus, directly or indirectly with antiviral ingredients (especially the ethanol) as well as by promoting and enabling the body's own immune system to better destroy, inactivate, and/or prevent the spread of the virus. Likewise, and again without wishing to be so limited by a specific theory, the inventor believes that the remedies prevent infection by destroying and/or inactivating virus with antiviral ingredients before the virus can begin to damage and replicate in tissues and/or by activating promoting and enabling the body's own immune system to better destroy, inactivate, and/or prevent the spread of the virus.

Particularly, the preparations of the invention are suitable for use any time from when the subject first notices any signs of a cold until the symptoms have cleared up. In fact, in some cases, such as for persistent sufferers, or where individually desired, it may be appropriate to continue treatment indefinitely, in the absence of contraindications. Thus, the remedies of the present invention are suitable for acute treatment, chronic treatment, and prophylaxis. Both acute and chronic treatment and prophylaxis will be encompassed by the term "treatment" for purposes of the present disclosure, unless indicated otherwise, either explicitly or from context. The terms "treatment" and "prophylaxis" are used in a broad sense, and extend from symptomatic relief to cure of the infection to general preventative therapy, especially in winter, or for particularly prone individuals.

A "subject in need of treatment" includes subjects who have contracted a virus which may cause a common cold, subjects who exhibit symptoms of the common cold, subjects who are suffering from a cold or from the symptoms of a cold, and those subjects who particularly wish to take preventative measures to avoid infection by a cold virus. Subjects who particularly wish to take preventative measures to avoid infection by a cold virus include those subjects who are or believe they are prone to infection by cold virus and those subjects who are especially vulnerable to suffering severe effects from a cold virus. The especial vulnerability of the latter population of subjects may be due to conditions including old age, young age, or immunocompromization. In the case of subjects who particularly wish to take preventative measures to avoid infection by a cold virus, the remedies of the present invention may be given as a prophylactic.

In order to test the efficacy of the cold repellant of the present invention, the inventor conducted 18 informal case studies and their results are provided in the Examples below. As can be seen from the Examples, in general, best results seem to be obtained when treatment is commenced immediately when there is any suspicion of a cold. Specifically, the cold and its accompanying cascade of cold symptoms is most effectively repelled by the remedy of the present invention when it is administered within the first 12 to 24 hours of the first cold symptom—most commonly, this first symptom is a sore throat.

When the remedies of the present invention are administered acutely, they are most preferably used beginning at the earliest signs of an oncoming cold. For example, a sore throat commonly indicates the onset of a cold. The remedy preferably is used three times per day (e.g., every 4–6 hours, preferably morning, midday, and evening). Preferably, the use of the remedy is continued for two days. However, the remedies may be used for longer periods, e.g., until the cold symptoms are completely gone. It is noted that in may cases, cold symptoms are alleviated or eliminated within two days after commencement of use of the remedy, and so two days is the recommended limit of administration because continued presence of symptoms may indicate a condition other than the common cold.

When the remedies of the present invention are administered prophylactically or chronically, they may be used at lower doses or with lower frequency than is desirable for acute administration.

The remedies of the present invention are preferably provided in a form that is not ingested into the digestive system, but instead facilitates contact between the active agents and the tissues in which the virus is present or through which the virus is likely to enter the body. A preferred form is a nasal spray. This form provides topical application of the medicaments to the nasal mucosa. Another form is in the topical application of the medicament in the form of a throat spray that applies to the oral pharyngeal area. A particularly preferred form is a mouthwash. Another particularly preferred form is a lozenge. These particularly preferred forms (mouthwash and lozenge) each provide topical application of the medicaments to the mouth and/or throat (specifically, the oral and oral pharyngeal mucosa).

The term "gargling" is to be interpreted broadly and encompasses gargling, swishing, simply holding liquid in the mouth and the back of the throat, and the like.

The remedy may also be administered in the form of a sublingual or buccal tablet, a syrup, or sublingual liquid drops or pastilles. These forms also provide for topical application of the medicaments to the mouth and/or throat.

The medicament is preferably maintained in contact with the mouth and/or throat for a sufficient length of time that reduction of the duration of the cold is achieved, reduction of the severity or presence of one or more symptoms of the cold is achieved, and/or prevention of infection by cold viruses is achieved. Maintenance of contact may preferably be achieved through the gargling of a mouthwash for a suitable length of time. Maintenance of contact may also preferably be achieved by the slow dissolution in the mouth of a suitably sized lozenge. Maintenance of contact may also be achieved by dissolving a suitable size or amount of, e.g., pastilles, drops, or sub-lingual or buccal tablets in the mouth.

The suitable length of contact, and thus the time of gargling, size of lozenge or tablet, or number of pastilles, is readily ascertainable to one of skill in the arts of homeopathy, herbal, and/or clinical medicine. Further, as with the concentrations of active ingredients to be employed (see above), the length of contact may differ with the characteristics of the subject and the object(s) to be achieved.

The remedy may also be administered in a form that is ingested into the digestive tract, such as tablets, capsules, and liquids; and may also be administered in the form of an injection or in a form absorbable through the skin.

Methods for formulating nasal sprays, throat sprays, mouthwashes, lozenges, sublingual tablets, buccal tablets, syrups, pastilles, drops, tablets, capsule, and liquids that are suitable carriers for medicaments are well known to the art of pharmaceutical formulation. One skilled in this art is also well aware of methods for preparing injectable forms of medicaments, as well as methods for preparing forms, such as skin-patches and creams, which allow for the absorption of medicaments through the skin.

The formulations may contain a predetermined amount or concentration of at least one medicament according to the present invention. These formulations can be prepared by any suitable pharmaceutical method. The formulations also may vary can vary with the condition and age of the patient and with the object(s) sought to be achieved. The amounts and/or concentrations of medicament to be included may be determined as indicated herein.

When formulating a mouthwash, lozenge, pastilles, or other form which is to be held in the mouth, it may be desirable to include at least one sweetener in the formulation. Examples of suitable sweeteners may be sugars such as fructose, lactose, and sucrose and sugar substitutes such as saccharin. Formulations to be held in the mouth may also desirably contain flavoring agents such as, for example, anise, anethole, eucalyptol, wintergreen, licorice, clove, cinnamon, spearmint, cherry, lemon, orange, lime, menthol, peppermint and various combinations thereof.

In formulations suitable for nasal administration, the ethanol, herbal, homeopathic, and, optionally, other active ingredients are formulated with a liquid carrier, such as those used in a conventional nasal spray or nasal drops.

In formulations suitable for throat administration, the ethanol, herbal, homeopathic, and, optionally, other active ingredients are formulated with a liquid carrier, such as those used in a conventional throat spray.

In a particularly preferred embodiment, the remedy is administered in the form of a mouthwash. Methods for making mouthwashes are well-known in the art. Non-limiting examples of mouthwash compositions, to which the ethanol (at sufficient concentrations) with or without herbal, homeopathic, and, optionally, other active ingredients may be added, are as follows.

| | |
|---|---|
| 0 to 2% | by weight of sodium saccharin, or an amount sufficient to provide a sweetening effect equivalent thereto of a sweetening agent; and |
| 0.01 to 1% | by weight flavoring agent (such as peppermint oil, spearmint oil, and/or mixtures thereof) |
| 20–95% | alcohol (ethanol) |
| q.s. | water |
| 5 to 15% v/v | sorbitol |
| 0.5 to 2.5% w/v | surfactant |
| 0.25 to 1% w/v | sodium chloride |
| 0.05 to 0.2% w/v | insoluble saccharin |
| 0.01 to .25% w/v | flavoring (such as menthol, thymol, eucalyptol, peppermint oil, and/or mixtures thereof) |
| 0.1 to 2% w/v | sodium ricinoleate |
| 20 to 95% v/v | alcohol (ethanol) |
| q.s. | water |

When the remedy is administered as a mouthwash formulation, it is most preferable if the subject does not swallow the mouthwash, but rather gargles with the solution deep in the throat, then spits out the solution. The mouth may be rinsed, if desired, but the throat is preferably not rinsed. Further, the subject preferably refrains from drinking any liquids for a period of at least one half hour or more after gargling.

In another particularly preferred embodiment the remedy administered in the form of a lozenge. Formulation of lozenges is well known in the art of pharmaceuticals. As an example, the herbal, homeopathic, and, optionally, other active ingredients may be mixed with a flavored base, usually sucrose and acacia or tragacanth and formulated into lozenges by standard methods.

In other embodiments, the remedy may be administered in the form of a sublingual or buccal tablet, a syrup, or sublingual liquid drops or pastilles. Methods of preparing such formulations are well-known in the art of pharmaceuticals.

In yet other embodiments, the remedy is administered in a form that is ingested into the digestive tract, such as tablets, capsules, and liquids. For example, the remedy may be administered in the form of gel capsules. It will be recognized that any known means of producing gel capsules can be used in accordance with the present invention. As another example, the remedy may be administered in the form of pressed tablets. Compressed tablets can be prepared by, for example, mixing the herbal, homeopathic, and, optionally, other active ingredients with dry inert ingredients such as carboxymethyl cellulose and compressing or molding in a suitable machine. The tablets optionally can be coated or scored and can be formulated so as to provide slow or controlled release of the active ingredients therein.

In still another embodiment, the remedy is administered in the form absorbable through the skin.

All publications and patent applications mentioned in this specification are herein incorporated by reference to the same extent as if each individual publication or patent application was specifically and individually indicated to be incorporated by reference.

EXAMPLES

In order to facilitate a more complete understanding of the invention, a number of Examples are provided below. However, the scope of the invention is not limited to specific embodiments disclosed in these Examples, which are for purposes of illustration only.

In each of the following examples, the subjects were administered one tablespoon (15 mL) of remedy comprising ethanol with or without homeopathic and/or herb ingredients adequately preserved in ethanol) consisting of one or a combination of *Allium cepa* (red onion), *Salvia officinalis* (Sage), *Sambucus nigra* (elderberry), Capsicum (cayenne fruit), *Mentha piperita* (peppermint), and/or *Thymus serpyllum* (thyme); and also comprising *Olea europaea* (olive whole leaf), *Lomatium dissectum* (lomatium root), *Rubis idaeus* (red raspberry leaf), and/or *Commiphora myrrha* (mrryh) in a mouthwash formulation three times a day for at least two days.

Example 1

The inventor, a female aged 38 at the time of this trial, administered the remedy to herself. She was suffering the symptoms of a common cold that was of 12 hours old duration at the time of the administration. The inventor's cold was blocked within 24 hours of treatment.

Example 2

The trial of Example 1 was again conducted when the inventor later suffered from an unrelated cold, and the cold was again blocked within 24 hours of treatment. At this time, the inventor was 39 years of age.

Example 3

The remedy was administered to a 26 year old male suffering from the symptoms of a common cold. The cold was blocked within 24 hours of treatment.

Example 4

The remedy was administered to a 21 year old male suffering from the symptoms of a common cold. The cold was blocked within 24 hours of treatment.

Example 5

The trial of Example 1 was again conducted when the inventor later suffered from an unrelated cold, and the cold was again blocked within 24 hours of treatment. At this time, the inventor was 40 years of age.

Example 6

The remedy was administered to a 35 year old female who had been suffering from a cold for a week before treatment. The woman's symptoms were so much reduced within 24 hours of treatment that she even visibly appeared to be recovering. In this case, 4 days passed before the symptoms were completely gone. The most likely reason that more time than in previous trials was required to completely clear the symptoms is that the cold had had 7 days to spread through the subject's body and affect many cells and tissues before treatment was begun.

Example 7

The remedy was administered to a 50 year old female who had been suffering from an especially severe cold for a week before treatment. The woman's symptoms were so much reduced within 24 hours of treatment that she even visibly appeared to be recovering. In this case, 4 days passed before the symptoms were completely gone. The most likely reason that more time than in previous trials was required to completely clear the symptoms is that the cold had had 7 days to spread through the subject's body and affect many cells and tissues before treatment was begun.

Example 8

The remedy was administered to a 40 year old male who had just begun suffering from the symptoms of a common cold. Although the symptoms had just begun to appear in the subject, the subject's son had been suffering from an especially severe cold for some time. Two strong doses were administered to this subject within 10 minutes, and the cold was blocked within 12 hours of treatment.

Example 9

The remedy was administered to an 11 year old male who had been suffering from the symptoms of a common cold for more than two days. The usual duration of the common cold in this subject is known to be 10 days. The cold during which this subject received the remedy of the present invention was reduced to 4 days total duration.

Example 10

The remedy was administered to a 48 year old male who had just begun suffering from the symptoms of a common cold. Although the symptoms had just begun to appear in the subject, the subject had just returned from a holiday during which he shared living quarters with several friends suffering from colds. The cold was blocked after one day following administration.

Example 11

The remedy was administered to a 37 year old female suffering from the symptoms of a common cold. This subject is known to be prone to numerous illnesses, and who often experiences relapses or reoccurrences of colds, often developing several colds in a row. The cold was blocked and she did not experience another reoccurrence until 4 weeks later.

Example 12

The remedy was administered to a 40 year old male suffering from the symptoms of a common cold. In this trial, the cold was not blocked. However, this subject is known to suffer from allergies and chronic sinusitis. Therefore, it is likely that an allergic reaction of bacterial infection was the cause of the symptoms.

Example 13

The remedy was administered to a 10 year old female suffering from the symptoms of a common cold. The cold was blocked.

Example 14

The remedy was administered to the subject of Example 11 when she later suffered from an unrelated cold, The cold was blocked with no reoccurance for at least 3 months.

Example 15

The remedy was administered to a 46 year old female who had just begun suffering from the symptoms of a common cold. The cold was blocked within 48 hours.

Example 16

The remedy was administered to the subject of Example 10 when he later began to suffer the symptoms of an unrelated cold, possibly spread by Example 15. The cold was blocked within 48 hours.

Example 17

The remedy was administered to a 50 year old male who had been severely suffering from the symptoms of a common cold for 12 hours. The cold was blocked within 24 hours.

Example 18

The remedy was administered to the subject of Example 17 when he later began to suffer the symptoms of an unrelated cold. Again the cold was blocked within 24 hours.

I claim:

1. An oral treatment method to reduce the duration of common cold symptoms, comprising:

administering to a patient suffering from the common cold an oral composition in a form suitable for gargling, said oral composition consisting essentially of 20–95% by volume aqueous ethanol, in an amount sufficient for the patient to gargle said composition, and further wherein said patient gargles the composition; and repeating the administration of said oral composition at least three times per day or at least every 4–6 hours for at least two days.

2. The oral treatment method according to claim 1 wherein said oral composition is a mouthwash.

3. The oral treatment method according to claim 1 wherein said oral composition comprises 27–40% by volume aqueous ethanol.

4. The oral treatment method according to claim 1 wherein said oral composition comprises about 31% by volume aqueous ethanol.

5. The oral treatment method according to claim 1 wherein said amount sufficient for said patient to gargle said composition is approximately 15 mL.

6. An oral treatment method to reduce the duration of common cold symptoms, comprising:

administering to a patient suffering from the common cold, with administration beginning within the first 12 to 24 hours of the first cold symptom, an oral composition in a form suitable for gargling, said oral composition consisting essentially of 20–95% by volume aqueous ethanol in an amount sufficient for the patient to gargle said composition, and further wherein said patient gargles the composition; and repeating the administration of said oral composition at least three times per day or at least every 4–6 hours for at least two days.

7. An oral treatment method to reduce the duration of common cold symptoms, comprising:

administering to a patient suffering from the common cold, with administration beginning within the first 12 to 24 hours of the first cold symptom, an oral composition in a form suitable for gargling, said oral composition consisting essentially of 20–95% by volume aqueous ethanol, wherein said aqueous ethanol is a food grade or consumer digestible ethanol or spirit ethanol, in an amount sufficient for the patient to gargle said composition, and further wherein said patient gargles the composition; and repeating the administration of said oral composition at least three times per day or at least every 4–6 hours for at least two days.

* * * * *

UNITED STATES PATENT AND TRADEMARK OFFICE
CERTIFICATE OF CORRECTION

| | | |
|---|---|---|
| PATENT NO. | : 6,641,801 B1 | Page 1 of 1 |
| APPLICATION NO. | : 09/821653 | |
| DATED | : November 4, 2003 | |
| INVENTOR(S) | : Amy Christine Brown | |

It is certified that error appears in the above-identified patent and that said Letters Patent is hereby corrected as shown below:

On The Title Page, Item (73) Assignee information reading "Love Lives, Honolulu, HI (US)" is deleted.

Signed and Sealed this
Tenth Day of February, 2015

Michelle K. Lee
*Deputy Director of the United States Patent and Trademark Office*